United States Patent [19]

Bonrath et al.

[11] Patent Number: 5,817,827

[45] Date of Patent: Oct. 6, 1998

[54] METHOD FOR THE DEHYDRATION OF AMIDES TO NITRILES

[75] Inventors: Werner Bonrath, Freiburg, Germany; Horst Pauling, Bottmingen, Switzerland

[73] Assignee: Hoffmann-La Roche Inc., Nutley, N.J.

[21] Appl. No.: 734,987

[22] Filed: Oct. 22, 1996

[30] Foreign Application Priority Data

Nov. 21, 1995 [CH] Switzerland .............................. 3290/95

[51] Int. Cl.⁶ ...................... C07D 263/34; C07D 211/78; C07C 253/00
[52] U.S. Cl. ............................ 546/286; 558/312; 548/236
[58] Field of Search ............................ 558/312; 548/236; 546/286

[56] References Cited

U.S. PATENT DOCUMENTS 2,783,264  2/1957  Klapproth et al. ...................... 558/312
4,908,452  3/1990  Claremon .

OTHER PUBLICATIONS

T. Rinderspacher and B. Prijs, Helv. Chim. Acta, 43, 1960, pp. 1522–1530.
Soviet Inventions Illustrated, Section Ch, Week 8243, Dec. 8, 1982.
Chemical Abstracts, vol. 86, No. 1, Jan. 3, 1977.

*Primary Examiner*—Johann Richter
*Assistant Examiner*—Joseph Murray
*Attorney, Agent, or Firm*—George W. Johnston; Patricia S. Rocha-Tramal

[57] ABSTRACT

The present invention relates to a process for the dehydration of amides to nitrites which comprises carrying out the dehydration in the presence of an adduct of sulphur trioxide and an amine as the dehydrating reagent in a basic reaction mixture. Thereby, for example, aliphatic, aromatic and heteroaromatic amides are dehydrated to the corresponding nitrites, such as 5-carbamoyl-4-methyl-oxazole to 5-cyano-4-methyl-oxazole, a valuable intermediate in the synthesis of pyridoxine.

11 Claims, No Drawings

METHOD FOR THE DEHYDRATION OF AMIDES TO NITRILES

The present invention is concerned with a novel process for the manufacture of nitrites by dehydrating the corresponding amides.

BACKGROUND OF THE INVENTION

Several processes for the manufacture of nitriles by dehydrating the corresponding amides have become known in the last few years. One of these known processes comprises, for example, carrying out the dehydration in the presence of phosphorus pentoxide [T. Rinderspacher and B. Prijs, Helv. Chim. Acta, 43, 1522–1530 (1960)]. The disadvantage of this process is, however, the low yield of product caused by the carbonization which occurs very readily in this reaction.

The object of the present invention is to provide a process for the manufacture of nitrites from amides by dehydration, in accordance with which the nitrile is obtained in a short reaction time, under mild reaction conditions and in high yield.

DETAILED DESCRIPTION OF THE INVENTION

The process in accordance with the invention comprises carrying out the dehydration in the presence of an adduct of sulphur trioxide and an amine in a basic reaction medium. The amine of this adduct is especially a tertiary amine.

Aliphatic amines as well as nitrogen-containing heteroaromatic compounds are suitable amines for the formation of the sulphur trioxide-amine adduct.

Among the aliphatic amines in the scope of the present invention there can be used especially trialkylamines with straight-chain or branched alkyl residues containing 1 to 20 carbon atoms. Examples of such alkyl residues are methyl, ethyl, n-propyl, isopropyl, n-butyl, isobutyl, tert.butyl, n-pentyl, n-hexyl and n-octyl. In such trialkylamines the alkyl residues can be the same or different. Examples of these trialkylamines—and at the same time preferred trialkylamines—are triethylamine and diisopropylethylamine, respectively.

The nitrogen-containing heteroaromatic compounds are especially heterocycles containing at least one ring nitrogen atom. Pyridine and pyridine derivatives, such as picoline and quinoline, are examples. Such nitrogen-containing heteroaromatic compounds can also be bonded to a polymeric carrier. Pyridine is the most preferred of these compounds. An example of pyridine bonded to a polymeric carrier is poly-(4-vinyl-pyridine); the adduct of which with sulphur trioxide is commercially available (Fluka Chemie AG, CH-9471 Buchs, Switzerland).

The use of the sulphur trioxide-amine adduct as the dehydrating reagent in the process in accordance with the invention is advantageous by virtue of its simple production from the educts sulphur trioxide and amine as well as the easier handling compared with the aggressive sulphur trioxide when this is used alone. The adducts are in part known and in some cases are commercially available. They can be produced readily by introducing sulphur trioxide into the diluted amine, methylene chloride, for example, being used as the diluent.

For the dehydration, the amide is reacted with the dehydrating reagent conveniently at room temperature, i.e. at about 25° C., or at elevated temperatures up to about 120° C., preferably at temperatures of about 50° C. to about 100° C., particularly at temperatures of about 70° C. to about 90° C.

The dehydration is carried out in a basic reaction medium. The same amines which are used for the formation of the dehydrating reagent can be used as the reaction medium. Dehydration with sulphur trioxide-triethylamine adduct in triethylamine has been found to be especially advantageous. If desired, a mixture of the amine with an organic solvent can be used as the reaction medium, with aliphatic or cyclic ethers, e.g. tert.butyl methyl ether or, respectively, tetrahydrofuran or dioxan, aliphatic nitriles, e.g. acetonitrile, or aromatic hydrocarbons, e.g. toluene, being especially suitable organic solvents. Preferably, however, no organic solvent is used.

When a solid amide is reacted, then the amide is conveniently suspended in the basic reaction medium.

The molar ratio of amide to dehydrating reagent is conveniently about 1:1 to about 1:10, preferably about 1:1 to about 1:4, especially about 1:1 to about 1:2.5.

After completion of the reaction the working up in order to obtain the crude product can be carried out according to appropriate methods used in organic chemistry. For the separation of the amine, the latter can, for example, be converted with hydrogen chloride into a hydrochloride, in which case the hydrogen chloride can be used as dilute hydrochloric acid (e.g. 25% hydrochloric acid), as concentrated hydrochloric acid or even as gaseous hydrogen chloride. The crude product can also be isolated by distillation.

The process in accordance with the invention enables nitriles to be manufactured from amides under mild reaction conditions and in high yields. It is suitable not only for the dehydration of aliphatic amides, but also of aromatic and heteroaromatic amides.

Straight-chain or branched alkylamides such as hexanamide, for example, can be used as aliphatic amides.

2-Naphthalenecarboxamide, benzamide and substituted benzamides, such as 4-chlorobenzamide or 3,5-difluorobenzamide, can for example be used as aromatic amides.

Nicotinamide can for example be used as the heteroaromatic amide.

The process is especially suitable for the manufacture of 5-cyano-4-lower alkyl-oxazoles, such as 5-cyano-4-methyl-oxazole, a valuable intermediate in the synthesis of pyridoxine (vitamin $B_6$).

The following Examples illustrate the process in accordance with the invention in more detail, but are not intended to represent any limitation.

EXAMPLE 1

Manufacture of 5-cyano-4-methyl-oxazole a) Dehydrating Reagent: triethylamine-sulphur trioxide A suspension of 200 mmol of 5-carbamoyl-4-methyl-oxazole and 500 mmol of triethylamine-sulphur trioxide in 200 ml of triethylamine was stirred at 89° C. for 6 hours.

For the working up, the reaction mixture, cooled to 0° C. in an ice bath, was treated with 150 ml of methyl tertiary butyl ether. For neutralization, concentrated hydrochloric acid was added dropwise until the pH value reached 7. The resulting precipitate was filtered off and washed with 100 ml of methyl tertiary butyl ether. The phases of the filtrate were separated and the aqueous phase was extracted twice with 50 ml of methyl tertiary butyl ether each time. The combined organic phases were washed once with saturated sodium bicarbonate solution and once with saturated sodium chloride solution, dried over anhydrous sodium sulphate and filtered. Finally, the filtrate was concentrated on a rotary evaporator at 40° C. and 500 mbar. Yield: 93% of theory, determined by gas chromatography.

b) Dehydrating Reagent: diisopropylethylamine-sulphur trioxide

A suspension of 200 mmol of 5-carbamoyl-4-methyl-oxazole and 500 mmol of diisopropylethylamine-sulphur trioxide in 200 ml of triethylamine was stirred at 89° C. for 6 hours. The working up was effected as described under a). Yield: 92% of theory.

c) Dehydrating Reagent: pyridine-sulphur trioxide

A suspension of 200 mmol of 5-carbamoyl-4-methyl-oxazole and 500 mmol of pyridine-sulphur trioxide in 200 ml of triethylamine was stirred at 89° C. for 6 hours. The working up was effected as described under a). Yield: 45% of theory.

EXAMPLE 2

Manufacture of Hexanonitrile

A suspension of 50 mmol of n-hexanamide and 125 mmol of triethylamine-sulphur trioxide in 75 ml of triethylamine was stirred at 89° C. for 6 hours. The working up was effected as described under Example 1a). Yield: 86% of theory.

EXAMPLE 3

Manufacture of 4-chlorobenzonitrile

A suspension of 50 mmol of 4-chlorobenzamide and 125 mmol of triethylamine-sulphur trioxide in 75 ml of triethylamine was stirred at 89° C. for 6 hours. The working up was effected as described under Example 1a). Yield: 92% of theory.

EXAMPLE 4

Manufacture of 3.5-difluorobenzonitrile

A suspension of 10 mmol of 3,5-difluorobenzamide and 25 mmol of triethylamine-sulphur trioxide in 30 ml of triethylamine was stirred at 89° C. for 1 hour. The working up was effected as described under Example 1a). Yield: 85.7% of theory.

EXAMPLE 5

Manufacture of naphthalene-2-carbonitrile

A suspension of 10 mmol of naphthalenecarboxamide and 25 mmol of triethylamine-sulphur trioxide in 30 ml of triethylamine was stirred at 89° C. for 2 hours. The working up was effected as described under Example 1a). Yield: 91% of theory.

EXAMPLE 6

Manufacture of 3-cyanopyridine

A suspension of 10 mmol of nicotinamide and 25 mmol of triethylamine-sulphur trioxide in 30 ml of triethylamine was stirred at 89° C. for 2 hours. The working up was effected as described under Example 1a). Yield: 95% of theory.

EXAMPLE 7

Manufacture of 5-ethoxy-4-methyloxazole-2-nitrile

A suspension of 10 mmol of 5-ethoxy-4-methyloxazole-2-carboxamide and 25 mmol of triethylamine-sulphur trioxide in 30 ml of triethylamine was stirred at 89° C. for 6 hours. The working up was effected as described under Example 1a). Yield: 76% of theory.

We claim:

1. A method for producing a nitrile which comprises dehydrating an amide with a sulfur trioxide-tertiary amine adduct in a basic reaction medium at a temperature of from about 25° C. to about 120° C. to obtain the nitrile.

2. The method of claim 1, wherein the molar ratio of the amide to the sulphur trioxide-amine adduct is from about 1:1 to about 1:10.

3. The method of claim 1, wherein the amide is selected from the group consisting of an aliphatic amide, an aromatic amide and a heteroaromatic amide.

4. The method of claim 2, wherein the temperature is from about 50° C. to about 100° C.

5. The method of claim 2, wherein the molar ratio is from about 1:1 to about 1:4.

6. The method of claim 4, wherein the amine is an aliphatic amine or a nitrogen-containing heteroaromatic compound.

7. The method of claim 4, wherein the amine is pyridine or a pyridine derivative.

8. The method of claim 4, wherein the amine is a trialkylamine wherein each alkyl residue contains from 1 to 20 carbon atoms.

9. The method of claim 4, wherein the temperature is from about 70° C. to about 90° C.

10. The method of claim 5, wherein the molar ratio is from about 1:1 to about 1:2.5.

11. The method of claim 3, wherein the amide is 5-carbamoyl-4-methyl-oxazole.

* * * * *